United States Patent [19]

Montgomery et al.

[11] 3,944,666

[45] Mar. 16, 1976

[54] INSECTICIDAL COMPOSITIONS AND METHODS OF COMBATTING INSECTS USING 3-PHENOXYBENZYL 2,2-DIMETHYL-3-(2,2-DICHLOROVINYL)-CYCLOPROPANECARBOXYLATE INSECTICIDE WITH A SYNERGISTIC COMPOUND OF MONO (ALKYL AND ALKENYL)MONO OMEGA-ALKYNYL ARYLPHOSPHONATES

[75] Inventors: Ronald Eugene Montgomery, Middleport; Harry Hobart Incho, Medina, both of N.Y.

[73] Assignee: FMC Corporation, Philadelphia, Pa.

[22] Filed: Nov. 15, 1974

[21] Appl. No.: 524,376

Related U.S. Application Data

[60] Continuation-in-part of Ser. No. 294,238, Oct. 2, 1972, Pat. No. 3,885,031, which is a division of Ser. No. 122,168, March 8, 1971, Pat. No. 3,709,988, which is a division of Ser. No. 800,264, Feb. 18, 1969, Pat. No. 3,652,741, which is a continuation-in-part of Ser. No. 630,204, April 12, 1967, abandoned, which is a continuation-in-part of Ser. Nos. 559,422, June 22, 1966, abandoned, and Ser. No. 624,689, March 21, 1967, abandoned.

[52] U.S. Cl. .............................. 424/219; 424/305
[51] Int. Cl.$^2$ ... A01N 9/02; A01N 9/24; A01N 9/36
[58] Field of Search ............................ 424/219, 305

[56] References Cited

UNITED STATES PATENTS

| | | | |
|---|---|---|---|
| 2,554,533 | 5/1951 | Ladd | 260/956 X |
| 3,065,125 | 11/1962 | Newallis | 424/219 |
| 3,212,964 | 10/1965 | Sehring et al. | 424/186 |
| 3,485,916 | 12/1969 | Neuneyer et al. | 424/186 |

OTHER PUBLICATIONS

Nature, 246, p. 169, (1973) Elliott et al.

*Primary Examiner*—Stanley J. Friedman
*Assistant Examiner*—Allen J. Robinson

[57] ABSTRACT

Synergistic insecticidal combinations of esters of certain cyclopropanecarboxylic acids, e.g. pyrethrins, allethrin, and related compounds, with mono(alkyl and alkenyl) mono-ω-alkynyl aryl- and aralkylphosphonates are described. The preparation and properties of representative members of this new class of synergistic phosphonates are described, and test results of their synergistic combinations with representative cyclopropanecarboxylates are reported.

12 Claims, No Drawings

INSECTICIDAL COMPOSITIONS AND METHODS OF COMBATTING INSECTS USING 3-PHENOXYBENZYL 2,2-DIMETHYL-3-(2,2-DICHLOROVINYL)-CYCLOPROPANECARBOXYLATE INSECTICIDE WITH A SYNERGISTIC COMPOUND OF MONO (ALKYL AND ALKENYL)MONO OMEGA-ALKYNYL ARYLPHOSPHONATES

CROSS REFERENCE TO RELATED APPLICATIONS:

This is a continuation-in-part of Ser. No. 294,238, filed Oct. 2, 1972, now U.S. Pat. No. 3,885,031, which is a division of Ser. No. 122,168, filed Mar. 8, 1971, now U.S. Pat. No. 3,709,988, which is a division of Ser. No. 800,264 filed Feb. 18, 1969, now U.S. Pat. No. 3,652,741, which is a continuation-in-part of Ser. No. 630,204 filed Apr. 12, 1967, now abandoned, which is a continuation-in-part of Ser. No. 559,422 filed June 22, 1966 and Ser. No. 624,689 filed Mar. 21, 1967, both now abandoned; and is related to copending applications Ser. No. 559,745 filed June 23, 1966, now U.S. Pat. No. 3,555,123 and Ser. No. 634,121 filed Apr. 27, 1967, now U.S. Pat. No. 3,557,259 which are continuations-in-part of Ser. No. 540,175 filed Apr. 5, 1966 and Ser. No. 559,412 filed June 22, 1966, respectively, both now abandoned.

BACKGROUND OF THE INVENTION:

Among the most widely used insecticides today are the pyrethrins, the active principle of pyrethrum flowers (*Chrysanthemum cinerariaefolium*), which have a high order of insecticidal activity and a low mammalian toxicity. The relatively high cost and the uncertain supply pf pyrethrins have encouraged attempts to prepare synthetic insecticides which retain the desirable properties of pyrethrins. It has long been known that synthetic products having a basic structural similarity to pyrethrins in that they are esters of certain substituted cyclopropanecarboxylic acids, in particular 2,2-dimethyl-3-(2-methylpropenyl)cyclopropanecarboxylic acid (which is also known as chrysanthemumic acid and will be so referred to herein), exhibit insecticidal activity of a significant order.

The wide market which pyrethrins and related synthetic insecticides enjoy today is due primarily to the discovery of certain additives which enhance the activity of these insecticides. These additives, commonly called synergists, are agents which may or may not themselves exhibit insecticidal activity, but which when combined with pyrethrins or related compounds produce new insecticides, having an effectiveness significantly greater than the sum of the effectiveness of the components when used separately. A great deal of time and effort has been devoted to the search for effective synergists. One of the most effective and most widely used of the pyrethrins synergists is the compound piperonyl butoxide, which is described in synergistic combination with pyrethrins in Wachs U.S. Pat. No. 2,550,737. Unfortunately, it has been found that many compounds which are excellent synergists for pyrethrins are not nearly as effective when used with allethrin or other synthetic cyclopropanecarboxylic acid esters.

SUMMARY OF THE INVENTION:

This invention relates to novel compositions for the control of insects and acarids and in particular to such pesticidal compositions containing pyrethrins, allethrin, or related insecticidal cyclopropanecarboxylic acid esters, in combination with certain mono(alkyl or alkenyl) mono-ω-alkynyl aryl- and aralkylphosphonates as synergists for insecticidal activity.

DESCRIPTION OF THE PREFERRED EMBODIMENTS

The synergistic phosphonates of this class have the structural formula:

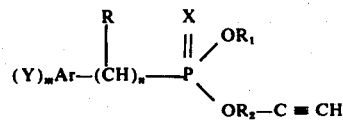

wherein $R_1$ is an alkyl, alkenyl, or alkoxyalkyl group of from one to about twenty carbon atoms, straight or branched chain; $R_2$ is an alkylene group of one to six carbon atoms, straight or branched chain; R is hydrogen or methyl; n is an integer from 0 to 3 inclusive; Ar is an aromatic radical such as phenyl, pyridyl, thienyl, pyrryl, furanyl, isothiazyl, and the corresponding benzoderivatives; Y is halogen; m is an integer from 0 to 2 inclusive; and X is oxygen or sulfur. When n is 2 or 3, the R groups may be the same or different. Similarly, when m is 2, the Y groups may be the same or different.

Particularly preferred are those compounds represented by the following formulae:

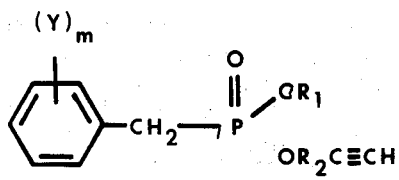 and 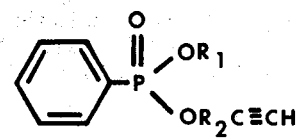

wherein $R_1$ is an alkyl or alkenyl group of from one to about six carbon atoms; $R_2$ is an alkylene group of from one to four carbon atoms; Y is chlorine or fluorine; and m is an integer from 0 to 2 inclusive.

Of the natural and synthetic esters of cyclopropanecarboxylic acids the best known members, preferred for use herein because of their general insecticidal activity and availability, are the esters of chrysanthemumic acid, which have the general structure:

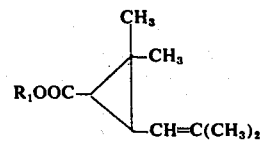

and wherein the radical $R_1$ can be any of the very large number of radicals which have been found to form insecticidal chrysanthemumates. For example, this cyclopentenyl)-2-methyl-4-oxo-2-cyclopentenyl chrysanthemumate) as described by Guest and Stansbury in U.S. Pat. No. 2,891,888; furethrin (3-furfuryl-2-methyl-4-oxo-2-cyclopentenyl chrysanthemumate) as described in National Distillers Products British Pat. No. 678,230; barthrin (6-chloropiperonyl chrysanthemumate) and its bromo analog, as described by Barthel et al in U.S. Pat. No. 2,886,485; dimethrin (2,4-dimethylbenzyl chrysanthemumate) and the 3,4-dimethyl isomer, as described by Barthel in U.S. Pat. No. 2,857,309; compounds of the class of (cyclohexene-1,2-dicarboximido)methyl chrysanthemumates as described in Belgian Pat. No. 646,399 and (cyclohexadiene-1,2-dicarboximido)methyl chrysanthemumates as described in Belgian Pat. No. 651,737, both to the Sumitomo Chemical Company, Ltd; and related compounds such as phthalimidoalkyl and substituted phthalimidoalkyl chrysanthemumates as described in Sumitomo Belgian Patent No. 635,902. Other insecticidal esters of chrysanthemumic acid also form synergistic combinations with the phosphonates of this invention.

Synthetic esters of other cyclopropanecarboxylic acids, closely related to chrysanthemumic acid, but having some variation in the substituents on the cyclopropane ring, have also been found to have insecticidal activity. Esters of this class are described in Netherlands Application No. 67,11587 to Sumitomo Chemical Company, Ltd. and in Belgian Pat. No. 690,984 to National Research Development Corporation. The useful insecticides of this class, which form synergistic combinations with the phosphonates of this invention, include esters of 2,2,3,3-tetramethylcyclopropanecarboxylic acid, particularly (5-benzyl-3-furyl)methyl 2,2,3,3-tetramethylcyclopropanecarboxylate.

More recently Elliott et al have reported highly active insecticidal cyclopropanecarboxylates arising from variations in the substituent at the 3-position of 2,2-dimethylcyclopropanecarboxylic acid, Nature, 244, 456 (1973), and 246, 169 (1973), including 3-phenyoxybenzyl 2,2-dimethyl-3-(2,2-dichlorovinyl)cyclopropanecarboxylate.

The preparation of the phosphonates of this invention and their synergistic insecticidal properties are illustrated in the following examples, which are not intended to be limitative of the variety of procedures which are applicable to the synthesis of mono(alkyl or alkenyl) mono-$\omega$-alkynyl phosphonates, or of the many insecticidal combinations in which they are effective. In these examples, all temperatures are in degrees centigrade.

EXAMPLE 1

Preparation of Butyl 3-Butynyl Phenylphosphonate

The starting material, butyl phenylphosphonochloridate, was prepared from dichlorophenylphosphine as follows: To a cold, stirred solution of 30.0 g of butanol and 41.4 g of trtiethylamine in about 300 ml of ethyl ether was added dropwise a solution of 34.6 g of dichlorophenylphosphine in about 200 ml of ethyl ether while the temperature was maintained below 0°. When addition was completed, the mixture was allowed to warm to room temperature. Stirring was continued overnight. The mixture was filtered, and the filtrate was concentrated under reduced pressure. The residual oil was distilled under reduced pressure to give 39.5 g of dibutyl phenylphosphonite, b.p. 120°–131°/ca 1.0 mm. class of esters includes the pyrethrins, allethrin (3-allyl-2-methyl-4-oxo-2-cyclopentenyl chrysanthemumate) and related insecticides as described by Schechter and La Forge in U.S. Pat. No. 2,661,374; cyclethrin (3-(2-Chlorine gas was bubbled into 38.5 g of dibutyl phenylphosphonite for about three hours. The mixture was warmed to 50° under aspirator vacuum to remove butyl chloride. The residual colorless oil was dissolved in 100 ml of benzene, washed with 1% sodium hydroxide and with water, dried over magnesium sulfate, and the dried solution concentrated under reduced pressure to give 30.6 g of pale yellow butyl phenylphosphonochloridate.

A solution of 15.6 g of butyl phenylphosphonochloridate in 15 ml of benzene was added dropwise with stirring to a cold solution of 5.2 g of 3-butyn-1-ol and 7.5 g of triethylamine in 45 ml of benzene while the temperature of the mixture was kept below 10°. When addition was complete, the mixture was slowly warmed to approximately 50° at which temperature it was stirred for one hour, then allowed to stand overnight at room temperature. The mixture was filtered, and the filtrate was washed with dilute hydrochloric acid, dilute sodium hydroxide, and water. The washed filtrate was dried over magnesium sulfate and concentrated under reduced pressure. The residue was distilled under reduced pressure to give 10.1 g of colorless butyl 3-butynyl phenylphosphonate. The stem and bath temperatures were 91°–106° and 130°–141° respectively with the pressure at 2 microns.

Analysis: Calc'd for $C_{14}H_{19}O_3P$: C, 61.41; H, 7.53; Found: C, 61.61; H, 7.55.

EXAMPLE 2

The Synergistic Activity of Butyl 3-Butynyl Phenylphosphonate

The synergistic insecticidal activity of butyl 3-butynyl phenylphosphonate in combination with representative insecticidal cyclopropanecarboxylates, e.g. chrysanthemumates, was determined by the following procedure: The test compound and the cyclopropanecarboxylate were dissolved in 70 parts by colume of acetone, which was then made up to 100 parts by volume by addition of water. A group of 30 to 40 houseflies (*Musca domestica L.*), immobilized under carbon dioxide, was placed on a moist filter paper on a Buchner funnel attached to a vacuum source. Twenty-five ml of test solution was poured over the immobilized flies, this being sufficient volume that all flies were completely immersed. Vacuum was then applied to remove the test solution, and the flies were transferred to holding cages lined with absorbent paper. Mortality counts were made after 24 hours. Results are shown in Table 1. In this and subsequent tables, the amounts of the test ingredients are stated in concentration terms of mg per 100 ml of test solution.

Table 1

| Synergistic Compositions of Butyl 3-Butynyl Phenylphosphonate | | | |
|---|---|---|---|
| Cyclopropanecarboxylate | mg | Synergist mg | Mortality of Houseflies |
| Allethrin | 10 | 50 | 100% |
|  | none | 50 | 38% |
|  | 10 | none | 34% |
| (1-Cyclohexene-1,2 dicarboximido)methyl chrysanthemumate | 10 | 50 | 100% |
|  | none | 50 | 38% |
|  | 10 | none | 28% |

The results in Table 1 illustrate the synergistic interaction of a phosphonate of this invention with two different synthetic chrysanthemumates.

EXAMPLE 3

The synergistic activity of butyl 3-butynyl phenylphosphonate with a variety of chrysanthemumate esters was evaluated against houseflies by the following procedure: About one microliter of a solution containing the indicated amount of the test materials in 100 ml of acetone was applied topically to each of 35 to 45 three- to four-day-old houseflies in one to four replicates. After 24 hours the mortality was determined by physical counting of the dead and living flies, and the percent kill was calculated. Results are shown in Table 2.

Table 2

| Compositions of Butyl 3-Butynyl Phenylphosphonate and Chrysanthemumates | | | |
|---|---|---|---|
| Chrysanthemumate | mg | Synergist mg | Mortality of Houseflies |
| Allethrin | 14.4 | 72 | 98% |
|  | none | 72 | 2% |
|  | 14.4 | none | 10% |
| Pyrethrins | 14.4 | 72 | 82% |
|  | none | 72 | 2% |
|  | 14.4 | none | 8% |
| (1-Cyclohexene-1,2 dicarboximido)methyl chrysanthemumate | 14.4 | 72 | 100% |
|  | none | 72 | 2% |
|  | 14.4 | none | 7% |

The results shown in Table 2 are illustrative of the general synergistic interaction between an alkyl $\omega$-alkynyl phenylphosphonate of this invention and chrysanthemumates. Even at dosages of 72 mg this phosphonate itself was essentially inactive, yet a consistent and substantial synergistic effect was observed in combinations with chrysanthemumates which themselves produced negligible kill of houseflies under these test conditions.

EXAMPLE 4

Preparation of Propyl 2-Propynyl Phenylphosphonate

Propyl phenylphosphinate used in the preparation of this synergist was prepared by the method of Kosolapoff, J.A.C.S. 72, 4292 (1950). Phenylphosphonous dichloride, 126.1 g, was added dropwise with stirring and cooling to 127 g propyl alcohol over a period of 30 minutes. The reaction mixture was allowed to warm to room temperature. After stirring at room temperature for 2 hours, the reaction mixture was warmed to 40°–50° and stirred for one hour. Excess propyl alcohol was removed under reduced presure (hot water bath), and the residual oil was vacuum distilled. The major cut, propyl phenylphosphinate, boiled at 103° at 3 mm. Hg. $n_D^{25}$ 1.5140. The total yield was 88 g of clear, colorless oil, identified by infrared spectral analysis.

A solution of 10.8 g propyl phenylphosphinate in 50 ml benzene was added dropwise to a chilled, stirred solution of 3.7 g 2-propyn-1-ol, 12.8 g bromotrichloromethane, and 7.1 g triethylamine in 100 ml benzene. During this addition the temperature was kept below 35°. When addition was complete, the reaction mixture was warmed to room temperature, and stirring was continued for 15 hours. Precipitated triethylammonium bromide was removed by filtration and the filtrate washed successively with dilute hydrochloric acid, dilute sodium hydroxide, and water. The washed organic layer was dried over magnesium sulfate, and after removal of the drying agent, stripped of solvent under reduced pressure, leaving 13.1 g of light yellow oil. The product was distilled (diffusion) with a bath temperature of 109°–118° at 0.1$\mu$ Hg. giving 10.4 g of propyl 2-propynyl phenylphosphonate as a clear, colorless oil.

Analysis: Calc'd for $C_{12}H_{15}O_3P$: C, 60.50; H, 6.35; P, 13.00; Found: C, 60.52; H, 6.53; P, 13.15.

EXAMPLE 5

The Synergistic Activity of Propyl 2-Propynyl Phenylphosphonate

The synergistic insecticidal activity of propyl 2-propynyl phenylphosphonate in combination with allethrin, pyrethrins, and (1-cyclohexene-1,2-dicarboximido)methyl chrysanthemumate was determined by the test procedure of Example 2. Results are shown in Table 3.

Table 3

| Compositions of Propyl 2-Propynyl Phenylphosphonate and Chrysanthemumates | | | |
|---|---|---|---|
| Chrysanthemumate | mg | Synergist mg | Mortality of Houseflies |
| Allethrin | 10 | 50 | 100% |
|  | none | 50 | 0 |
|  | 10 | none | 8% |
| Pyrethrins | 10 | 50 | 100% |
|  | none | 50 | 0 |
|  | 10 | none | 3% |
| (1-Cyclohexene-1,2 dicarboximido)methyl chrysanthemumate | 10 | 50 | 100% |
|  | none | 50 | 0 |
|  | 10 | none | 12% |

Table 3 shows that propyl 2-propynyl phenylphosphonate, itself inactive at the dosage used, is an effective synergist for a variety of chrysanthemumates.

EXAMPLE 6

The synergistic activity of propyl 2-propynyl phenylphosphonate with a variety of chrysanthemumate esters against houseflies was further demonstrated using the test procedure of Example 3. Results are shows in Table 4.

Table 4

| Compositions of Propyl 2-Propynyl Phenylphosphonate and Chrysanthemumates | | | |
|---|---|---|---|
| Chrysanthemumate | mg | Synergist mg | Mortality of Houseflies |
| Allethrin | 14.4 | 72 | 71% |
|  | none | 72 | 4% |
|  | 14.4 | none | 10% |
| Pyrethrins | 14.4 | 72 | 84% |
|  | none | 72 | 4% |
|  | 14.4 | none | 8% |
| (1-Cyclohexene-1,2-dicarboximido)methyl chrysanthemumate | 14.4 | 72 | 100% |
|  | none | 72 | 4% |
|  | 14.4 | none | 7% |

EXAMPLE 7

Preparation of sec-Butyl 2-Propynyl Phenylphosphonate

The intermediate sec-butyl phenylphosphinate was prepared as follows: Under a nitrogen atmosphere 25.9 g phenylphosphonous dichloride was added dropwise with stirring to 32.2 g sec-butyl alcohol. During the 20 minute period of addition the reaction mixture was held at 5°–10°. The mixture was allowed to warm to room temperature and was stirred overnight. Excess sec-butyl alcohol was removed under reduced pressure to yield 27.8 g sec-butyl phenylphosphinate, identified by infrared spectral analysis.

A solution of 10.0 g sec-butyl phenylphosphinate in 20 ml benzene was added dropwise to a stirred solution of 3.4 g 2-propyn-1-ol, 9.4 g carbon tetrachloride, and 6.2 g triethylamine in 100 ml benzene. During addition the reaction mixture was kept at 15°–20°, then allowed to warm to room temperature and stirred overnight. Precipitated triethylammonium chloride was removed by filtration and the filtrate washed successively, twice with 1% hydrochloric acid, once with 0.5% sodium hydroxide, and twice with water. The washed organic layer, dried over magnesium sulfate, was stripped of solvent under reduced pressure and then subjected to high vacuum with vigorous stirring at room temperature for six hours. The resulting oil, 8.0 g, identified as sec-butyl 2-propynyl phenylphosphonate by infrared spectroscopy, was 98% pure by vapor phase chromatography.

Analysis: Calc'd for $C_{13}H_{17}O_3P$: C, 61.89; H, 6.79; P 12.28; Found: C, 62.10; H, 6.77; P 12.31.

EXAMPLE 8

Preparation of Isobutyl 2-Propynyl Phenylphosphonate

Following the procedure described in Example 7, 25.9 g phenylphosphonous dichloride was reacted with 32.2 g isobutyl alcohol to yield 28.7 g isobutyl phenylphosphinate. The intermediate phosphinate, 10.0 g was reacted with 3.4 g 2-propyn-1-ol, 9.4 g carbon tetrachloride, and 6.2 g of triethyl amine. Vapor phase chromatography showed the product to be 98% pure. Distillation in a short path still (diffusion pump, bath temperature 108°–121°) gave fractions containing from 97.8 to 99.5% of isobutyl 2-propynyl phenylphosphonate, identified by infrared spectral analysis, for a total yield of 8.0 g.

Analysis: $C_{13}H_{17}O_3P$: C, 61.89; H, 6.79; P, 12.28; Found: C, 61.68; H, 6.71; P, 12.05.

EXAMPLE 9

Preparation of Ethyl 4-Pentynyl Phenylphosphonate

Following the procedure described in Example 1, 5.85 g 4-pentyn-1-ol was reacted with 11.3 g ethyl phenylphosphonochloridate. The final product, ethyl 4-pentynyl phenylphosphonate, distilled (diffusion system) at a bath temperature of 120°–130° at 0.01 mm Hg.

Analysis: Calc'd for $C_{13}H_{17}O_3P$: C, 61.90; H, 6.79; P, 12.28; Found: C, 61.65; H, 7.04; P, 12.17.

EXAMPLE 10

Preparation of n-Butyl 3-Butynyl 2-Thienylphosphonate

Following the procedure described in Example 4, 4.0 g of 3-butyn-1-ol was reacted with 10.3 g of n-butyl 2-thienylphosphinate. The product, n-butyl 3-butynyl 2-thienylphosphonate, was distilled in short path diffusion apparatus at 0.5μHg. with a bath temperature of 128°–140°. $n_D^{25}$ 1.5069.

Analysis: Calc'd for $C_{12}H_{17}O_3PS$: C, 52.93; H, 6.29; P, 11.37; Found: C, 53.22; H, 6.46; P, 11.48.

EXAMPLE 11

Preparation of n-Octadecyl 3-Butynyl Phenylphosphonate

Following the procedure of Example 4, 12.6 g 3-butynyl phenylphosphinate was reacted with 17.4 g n-octadecanol. The product, n-octadecyl 3-butynyl phenylphosphonate, recrystallized from hexane, was a waxy solid, partially molten at room temperature.

Analysis: Calc'd for $C_{28}H_{47}O_3P$: C, 72.69; H, 10.24; P, 6.69; Found: C, 72.74; H, 10.33; P, 6.58.

EXAMPLE 12

Preparation of Propyl 2-Propynyl Benzylphosphonate

The intermediate 2-propynyl benzylphosphonochloridate was prepared through a series of reactions starting with diethyl benzylphosphonate as set forth below.

In a flask equipped with heating mantle, stirrer, and reflux condenser were combined 1000 g diethyl benzylphosphonate and 3.8 liters of 12N hydrochloric acid. After the stirred mixture was heated to 65°, enough dioxane (200–210 ml) was added to give a clear solution. The solution was stirred and refluxed for 64 hours. When the solution was cooled to 45°–50°, a solid separated out. The filtered solid was dried in a vacuum oven at 70°–74° for 15 hours, giving a yield of 703 g benzylphosphonic acid, m.p. 171°–173°.

In a flask equipped with a stirrer, reflux condenser, drying tube, solid addition funnel, and gas scrubber, a slurry of 111.5 g benzylphosphonic acid in 1 l hexane was stirred and warmed to 35°–40°. When the first 50 g portion of a total of 259 g $PCl_5$ was added to the mixture, reaction started immediately as evidenced by evolution of HCl. The reaction mixture was then cooled to room temperature, and the balance of the $PCl_5$ added in 50 g portions over a period of about 2 hours, during which time the temperature increased to 60°. After the reaction mixture cooled to room temperature, $SO_2$ was bubbled through the mixture for fifteen minutes to remove HCl. After removal of solvent under reduced pressure, the product was distilled in a short path still (pressure 0.01 mm., pot temperature 85°–125°) to give 123.7 g benzylphosphonic dichloride.

Dipropyl benzylphosphonate was prepared by dropwise addition of 62 g benzylphosphonic dichloride in 200 ml benzene to a stirred solution of 39.3 g n-propyl alcohol and 65.9 g triethylamine in 400 ml benzene. After stirring overnight the reaction mixture was filtered to remove triethylammonium chloride. The filtered solid was washed with benzene, and the washings added to the filtrate. The clear benzene solution was washed four times with 100 ml portions of 1% hydrochloric acid, twice with 100 ml portions of 1% sodium hydrozide, and finally with 100 ml water. The solution was then dried over magnesium sulfate. After removal of solvent under reduced pressure, the product was distilled in a short path still (pressure 0.06 mm., bath temperature 115°–128°) to give a total yield of 47 g dipropyl benzylphosphonate, $n_D^{25}$ 1.4883, identified by infrared spectral analysis.

Analysis: Calc'd for $C_{13}H_{21}O_3P$: C, 60.93; H, 8.26; P, 12.09; Found: C, 60.97; H, 8.18; P, 12.27.

Propyl benzylphosphonate was prepared from the intermediate dipropyl ester as follows: 45 g dipropyl benzylphosphonate 39 g soldium hydroxide, and 350 ml distilled water were stirred at reflux temperature for 20 hours, during which period the cloudy reaction mixture became clear. When the pH was adjusted to 1 by dropwise addition of about 125 ml concentrated hydrochloric acid, a solid precipitate formed. Since the solid liquified during an attempt at filtration, the product was taken into solution by three successive extractions of the reaction mixture with 200 ml portions of chloroform. After the combined extracts were dried over magnesium sulfate, solvent was removed under reduced pressure to give a viscous, cloudy liquid. Further subjection to vacuum gave 37.5 g of sticky, white solid, propyl benzylphosphonate, used in the following synthesis step.

Propyl benzylphosphonochloridate was prepared as follows: Under a nitrogen atmosphere, in a flask equipped with a stirrer, gas inlet tube, condenser, and gas scrubber, 37.5 g propyl benzylphosphonate and 94 g thionyl chloride were stirred at 40°–50° for 4½ hours. To aid in the removal of any volatile by-products, two successive 100 ml portions of benzene were added to the reaction mixture at room temperature and then removed under reduced pressure. Further subjection to vacuum gave 40.4 g of amber colored liquid, identified by infrared spectroscopy as propyl benzylphosphonochloridate.

The synergist propyl 2-propynyl benzylphosphonate was prepared as follows: In a flask equipped with a stirrer, a condenser fitted with a drying tube, and a dropping funnel, 20.5 g propyl benzylphosphonochloridate in 50 ml benzene was added dropwise, over a period of 30 minutes, to a stirred solution of 5.5 g 2-propyn-1-ol and 9.8 g triethylamine in 100 ml benzene. After stirring at room temperature for about 15 hours, the solution was filtered free of triethylammonium chloride, and washed twice with 50 ml 1% sodium hydroxide and once each with 50 ml 1% hydrochloric acid and 50 ml water. The solution was dried over magnesium sulfate and the solvent removed under reduced pressure to give an amber colored oil. The crude product was distilled in a molecular still (0.0001–0.00015 mm Hg, bath temperature 120°C) to give 14.5 g propyl 2-propynyl benzylphosphonate, a lemon colored oil, $n_D^{25}$ 1.5074.

Analysis: Calc'd for $C_{13}H_{17}O_3P$: C, 61.90; H, 6.79; P, 12.28; Found: C, 61.81; H, 6.80; P, 12.16.

EXAMPLE 13

Preparation of Propyl 3-Butynyl Benzylphosphonate

Following the procedure of Example 12, 19.9 g propyl benzylphosphonochloridate was reacted with 6.6 g of 3-butyn-1-ol and 9.5 g triethylamine to give 15.6 g propyl 3-butynyl benzylphosphonate, identified by infrared spectral analysis, $n_D^{25}$ 1.5052.

Analysis: calc'd for $C_{14}H_{19}O_3P$: C 63.15; H 7.19; P 11.63; Found: C 63.04; H 7.46; P 11.63.

EXAMPLE 14

Preparation of Ethyl 2-Propynyl Benzylphosphonate

The procedure of Example 12 was used to prepare ethyl 2-propynyl benzylphosphonate, identified by infrared spectral analysis, $n_D^{25}$ 1.5124.

Analysis: Calc'd for $C_{12}H_{15}O_3P$: C 60.50; H 6.35; P 13.00; Found: C 60.56; H 6.45; P 12.73.

EXAMPLE 15

Preparation of Ethyl 2-Propynyl 4-Chlorobenzylphosphonate

The procedure of Example 12 was followed except that in the present example the unsaturated alcohol was reacted with the phosphonate moiete first, and the saturated alcohol was reacted second. Thus 4-chlorobenzylphosphonic dichloride was converted to di-2-propynyl 4-chlorobenzylphosphonate, and in the last step 2-propynyl 4-chlorobenzylphosphonochloridate was reacted with ethyl alcohol to give ethyl 2-propynyl 4-chlorobenzylphosphonate, identified by infrared spectral analysis, $n_D^{25}$ 1.5218.

Analysis: Calc'd for $C_{12}H_{14}ClO_3P$: C 52.86; H 5.18; P 11.36; Found: C 53.14; H 5.36; P 11.15.

EXAMPLE 16

Preparation of Propyl 2-Propynyl 4-Chlorobenzylphosphonate

Following the procedure of Example 15, 2-propynyl 4-chlorobenzylphosphonochloridate was reacted with n-propyl alcohol to give propyl 2-propynyl 4-chlorobenzylphosphonate, identified by infrared spectral analysis, $n_D^{25}$ 1.5174.

Analysis: Calc'd for $C_{13}H_{16}ClO_3P$: C 54.46; H 5.63; P 10.80; Found: C 53.72; H 5.81; P 11.14.

EXAMPLE 17

Preparation of Propyl 2-Propynyl 3,4-Dichlorobenzylphosphonate

The procedure of Example 12 was followed except that 3,4-dichlorobenzylphosphonic dichloride was prepared by the reaction of phosphorus pentachloride (505 g) with the diethyl ester of 3,4-dichlorobenzylphosphonic acid (304 g) rather than with the free acid. The final product, propyl 2-propynyl 3,4-dichlorobenzylphosphonate, was identified by infrared spectral analysis, $n_D^{25}$ 1.5305.

Analysis: Calc'd for $C_{13}H_{15}Cl_2O_3P$: C 48.62; H 4.71; P 9.64; Found: C 48.34; H 4.50; P 9.54.

EXAMPLES 18 TO 43

Following the general procedures exemplified above, a large number of compounds of this class are readily synthesized. The synergistic activity of typical phosphonates of this invention, in combination with typical and useful insecticidal cyclopropanecarboxylates is further illustrated in Table 5. These results were obtained following the procedure described in Example 2.

Table 5.

| | Synergistic Insecticidal Compositions | | | |
|---|---|---|---|---|
| Cyclopropanecarboxylate | mg | Phosphonate | mg | Mortality of Houseflies |
| (1-Cyclohexene-1,2-dicarboximido)methyl chrysanthemumate | 10 | Methyl 2-propynyl phenylphosphonate | 50 | 100% |
|  | none |  | 50 | 0 |
|  | 10 |  | none | 11% |
| Pyrethrins | 10 | Methyl 3-butynyl phenylphosphonate | 50 | 100% |
|  | none |  | 50 | 20% |
|  | 10 |  | none | 3% |
| Allethrin | 10 | Ethyl 3-butynyl phenylphosphonate | 50 | 100% |
|  | none |  | 50 | 36% |
|  | 10 |  | none | 8% |
| Allethrin | 10 | Ethyl 4-pentynyl | 50 | 79% |

Table 5.-continued

Synergistic Insecticidal Compositions

| Cyclopropanecarboxylate | mg | Phosphonate | mg | Mortality of Houseflies |
|---|---|---|---|---|
| | none | phenylphosphonate | 50 | 0 |
| | 10 | | none | 8% |
| Pyrethrins | 10 | Ethyl 3-butynyl benzylphosphonate | 50 | 100% |
| | none | | 50 | 7% |
| | 10 | | none | 3% |
| Pyrethrins | 10 | Ethyl 4-pentynyl benzylphosphonate | 50 | 100% |
| | none | | 50 | 38% |
| | 10 | | none | 3% |
| Allethrin | 10 | Ethyl 3-butynyl 4-fluorobenzyl-phosphonate | 50 | 100% |
| | none | | 50 | 8% |
| | 10 | | none | 8% |
| (1-Cyclohexene-1,2-dicarboximido)methyl chrysanthemumate | 10 | n-Propyl 3-butynyl phenylphosphonate | 50 | 100% |
| | none | | 50 | 12% |
| | 10 | | none | 12% |
| Pyrethrins | 10 | n-Propyl 4-pentynyl phenyl-phosphonate | 50 | 100% |
| | none | | 50 | 3% |
| | 10 | | none | 3% |
| Allethrin | 10 | i-Propyl 2-propynyl phenyl-phosphonate | 50 | 100% |
| | none | | 50 | 0 |
| | 10 | | none | 33% |
| (1-Cyclohexene-1,2-dicarboximido)methyl chrysanthemumate | 10 | 2-Propenyl 2-propynyl phenyl-phosphonate | 50 | 100% |
| | none | | 50 | 3% |
| | 10 | | none | 11% |
| Pyrethrins | 10 | 2-Propenyl 3-butynyl phenyl-phosphonate | 50 | 95% |
| | none | | 50 | 0 |
| | 10 | | none | 7% |
| (1-Cyclohexene-1,2-dicarboximido)methyl chrysanthemumate | 10 | n-Butyl 3-butynyl 2-thienylphosphon-ate | 50 | 100% |
| | none | | 50 | 26% |
| | 10 | | none | 24% |
| (1-Cyclohexene-1,2-dicarboximido)methyl chrysanthemumate | 10 | n-Pentyl 2-propynyl phenyl-phosphonate | 50 | 100% |
| | none | | 50 | 19% |
| | 10 | | none | 28% |
| Allethrin | 10 | n-Pentyl 3-butynyl phenylphosphonate | 50 | 100% |
| | none | | 50 | 0 |
| | 10 | | none | 39% |
| (1-Cyclohexene-1,2-dicarboximido)methyl chrysanthemumate | 10 | n-Pentyl 4-pentynyl phenyl-phosphonate | 50 | 100% |
| | none | | 50 | 0 |
| | 10 | | none | 28% |
| Allethrin | 10 | n-Dodecyl 3-butynyl phenyl-phosphonate | 50 | 84% |
| | none | | 50 | 3% |
| | 10 | | none | 33% |
| Allethrin | 10 | n-Octadecyl 3-butynyl phenyl-phosphonate | 50 | 93% |
| | none | | 50 | 10% |
| | 10 | | none | 19% |
| Pyrethrins | 10 | sec-Butyl 2-propynyl phenyl-phosphonate | 50 | 100% |
| | none | | 50 | 7% |
| | 10 | | none | 31% |
| Pyrethrins | 10 | Isobutyl 2-propynyl phenyl-phosphonate | 50 | 100% |
| | none | | 50 | 0 |
| | 10 | | none | 31% |
| Allethrin | 10 | n-Propyl 2-propynyl benzyl-phosphonate | 50 | 100% |
| | none | | 50 | 4% |
| | 10 | | none | 7% |
| Pyrethrins | 10 | n-Propyl 3-butynyl benzyl-phosphonate | 50 | 100% |
| | none | | 50 | 3% |
| | 10 | | none | 21% |
| (1-Cyclohexene-1,2-dicarboximido)methyl chrysanthemumate | 10 | Ethyl 2-propynyl benzyl-phosphonate | 50 | 100% |
| | none | | 50 | 3% |
| | 10 | | none | 35% |
| Allethrin | 10 | Ethyl 2-propynyl 4-chlorobenzyl-phosphonate | 50 | 100% |
| | none | | 50 | 0 |
| | 10 | | none | 3% |
| Pyrethrins | 10 | n-Propyl 2-propynyl 4-chlorobenzyl-phosphonate | 50 | 100% |
| | none | | 50 | 3% |
| | 10 | | none | 11% |
| (1-cyclohexene-1,2-dicarboximido)methyl chrysanthemumate | 10 | n-Propyl 2-propynyl 3,4-dichloro-benzylphosphonate | 50 | 100% |
| | none | | 50 | 10% |
| | 10 | | none | 35% |

EXAMPLE 44

The synergistic activity of the phosphonates of this invention with chrysanthemumates over a wide range of chrysanthemumate to synergist ratios was demonstrated by a series of tests carried out by the method described in Example 2. Results for two different chrysanthemumate-synergist combinations are shown in Table 6.

Table 6

Compositions With Different Chrysanthemumate To Synergist Ratios

| mg. Chrysan-themumate(-A) | mg. Synergist(B) | Ratio A:B | Mortality of Houseflies | |
|---|---|---|---|---|
| | | | composition I | Composition II |
| 5 | none | — | 9% | 13% |
| 5 | 10 | 1:2 | 83% | 61% |
| 5 | 25 | 1:5 | 100% | 78% |
| 5 | 50 | 1:10 | 100% | 97% |
| 5 | 100 | 1:20 | 100% | 100% |

Table 6-continued
Compositions With Different Chrysanthemumate To Synergist Ratios

| mg. Chrysan-themumate(-A) | mg. Synergist(B) | Ratio A:B | Mortality of Houseflies | |
|---|---|---|---|---|
| | | | composition I | Composition II |
| 5 | 250 | 1:50 | 100% | 100% |
| none | 100 | — | 8% | 23% |
| none | 250 | — | 3% | 41% |

Composition I: Chrysanthemumate — (1-cyclohexene-1,2-dicarboximido)methyl chrysanthemumate
Synergist — propyl 2-propynyl phenyl-phosphonate
Composition II: Chrysanthemumate — allethrin
Synergist — butyl 3-butynyl phenyl-phosphonate The results in Table 6 illustrate the marked synergistic interaction found over a wide range of ratios.

EXAMPLE 45

Synergistic activity over a wide range of cyclopropanecarboxylate to synergist ratios was further demonstrated by a series of tests of representative phosphonates of the invention with (5-benzyl-3-furyl)-methyl 2,2,3,3-tetramethylcyclopropanecarboxylate. The test method was as described in Example 2, but with lower concentrations owing to the high level of activity of the cyclopropanecarboxylate. Results are shown in Table 7.

Table 7
(5-Benzyl-3-furyl)methyl 2,2,3,3-Tetramethylcyclopropanecarboxylate in Synergistic Compositions

| mg. Cyclopropane-carboxylate (A) | mg. Synergist (B) | Mortality of Houseflies | | |
|---|---|---|---|---|
| | | A only | B only | A+B |
| Synergist I: | | | | |
| 1.0 | 5 | 60 | 0 | 100 |
| .5 | 5 | 54 | 0 | 98 |
| .2 | 10 | 0 | 0 | 58 |
| .2 | 20 | 0 | 42 | 100 |
| Synergist II: | | | | |
| .5 | 5 | 54 | 0 | 88 |
| .2 | 10 | 0 | 0 | 65 |
| .2 | 20 | 0 | 0 | 95 |
| Synergist III: | | | | |
| .5 | 5 | 54 | 0 | 74 |
| .2 | 10 | 0 | 0 | 94 |
| .2 | 20 | 0 | 22 | 100 | synergist I: Propyl 2-propynyl phenylphosphonate
Synergist II: Isobutyl 2-propynyl phenylphosphonate
Synergist III: Propyl 3-butynyl benzylphosphonate

EXAMPLE 46

The synergistic interaction of a phosphonate synergist of this invention with 3-phenoxybenzyl 2,2-dimethyl-3-(2,2-dichlorovinyl)cyclopropanecarboxylate is exemplified below. About one microliter of a solution containing the equivalent of the indicated amount of the test materials in 100 ml of acetone was applied topically to each of 12–20 three- to four-day-old houseflies in each of four to five replicates for each concentration. After 24 hours the mortality was determined by physical counting of the dead and living flies, and the percent kill was calculated. Results are shown in Table 8.

Table 8
3-Phenoxybenzyl 2,2-Dimethyl-3-(2,2-dichlorovinyl)-cyclopropanecarboxylate in Synergistic Compositions.

| mg-Cyclopropane-carboxylate (A) | mg. Synergist (B) | Mortality of Houseflies[1] |
|---|---|---|
| 1.3 | 6.5 | 8,5% |
| 1.8 | 9.0 | 11,16% |
| 2.5 | 12.5 | 26,27% |
| 3.5 | 17.5 | 53,57% |
| 2.5 | — | 6% |
| 3.5 | — | 16% |
| 5.0 | — | 40% |
| 7.0 | — | 54% |
| — | 50 | 0,4% |

(A) 3-phenoxybenzyl 2,2-dimethyl-3-(2,2-dichlorovinyl)cyclopropanecarboxylate.
(B) isobutyl 2-propynyl phenylphosphonate
[1]There were 2 tests of four to five replicates each where two numbers are shown.

EXAMPLE 47

In the manner described in Example 46, synergistic compositions were studied in which the ratio of 3-phenoxybenzyl 2,2-dimethyl-3-(2,2-dichlorovinyl)cyclopropanecarboxylate to isobutyl 2-propynyl phenylphosphonate was varied. Results are shown in Table 9.

Table 9
Synergistic Compositions with Different Insecticide to Synergist Ratios

| mg Cyclopropane-carboxylate (A) | mg Synergist (B) | Ratio A:B | Mortality of Houseflies |
|---|---|---|---|
| 4.0 | none | — | 22% |
| 5.4 | none | — | 33% |
| 7.2 | none | — | 43% |
| 9.6 | none | — | 71% |
| 13.0 | none | — | 82% |
| 4.0 | 2.0 | 1:0.5 | 37% |
| 5.4 | 2.7 | 1:0.5 | 53% |
| 7.2 | 3.6 | 1:0.5 | 59% |
| 4.5 | 5.63 | 1:1.25 | 78% |
| 5.4 | 6.75 | 1:1.25 | 73% |
| 7.0 | 8.75 | 1:1.25 | 89% |
| 10.0 | 12.50 | 1:1.25 | 99% |
| 3.5 | 8.75 | 1:2.5 | 64% |
| 4.0 | 10.0 | 1:2.5 | 83% |
| 5.2 | 13.0 | 1:2.5 | 86% |
| 5.4 | 13.5 | 1:2.5 | 91% |
| 3.0 | 15.0 | 1:5 | 84% |
| 3.2 | 16.0 | 1:5 | 75% |
| 4.0 | 20.0 | 1:5 | 92% |
| 1.5 | 15.0 | 1:10 | 24% |
| 2.2 | 22.0 | 1:10 | 63% |
| 1.00 | 20.0 | 1:20 | 17% |
| 1.50 | 30.0 | 1:20 | 68% |
| none | 50 | — | 0,4% |

(A) 3-phenoxybenzyl 2,2-dimethyl-3-(2,2-dichlorovinyl)cyclopropanecarboxylate.
(B) isobutyl 2-propynyl phenylphosphonate

EXAMPLE 48

The effectivness of the synergistic compositions of this invention is strikingly shown in aerosol formulations, as illustrated in the following example: Aerosol formulations were prepared containing a typical insecticidal chrysanthemumate, both with and without the synergist, in this example butyl 3-butynyl phenylphosphonate, as follows:

| | With Synergist | Without Synergist |
|---|---|---|
| (1-Cyclohexene-1,2-dicarboximido)-methyl chrysanthemumate (90% active) | 0.140 g | 0.140 g |
| Butyl 3-butynyl phenylphosphonate | 0.625 g | none |

-continued

| | With Synergist | Without Synergist |
|---|---|---|
| Heavy aromatic naphtha | 6.00 g | 6.00 g |
| Purified kerosene | 3.24 g | 3.86 g |
| Trichloromonofluoromethane | 20.00 g | 20.00 g |
| Dichlorodifluoromethane | 20.00 g | 20.00 g |

A group of 200 to 300 houseflies was introduced into a 216 cu. ft. test chamber, prepared according to the specifications of the Chemical Specialties Manufacturers Association (Soap and Chemical Specialties, 1961 Blue Book, p. 244). Measured amounts of the aerosol formulations were introduced into the chamber. Results, shown in Table 10 are the averages of nine replicates for the composition containing the synergist and of two replicates for the composition containing the chrysanthemumate alone.

Table 10.

| | Aerosol Formulations | | |
|---|---|---|---|
| Composition | Average Dose (g/1000ft$^3$) | Knockdown 15 minutes | Mortality 24 hours |
| With Synergist | 3.15 g | 84% | 71% |
| Without Synergist | 2.92 g | 85% | 14% |

It is of particular interest to note that butyl 3-butynyl phenylphosphonate enhanced to a marked extent the percent kill obtained with this chrysanthemumate, which by itself exhibited excellent knockdown of houseflies, but very poor permanent effectiveness.

In addition to the specific phosphonates exemplified herein, similar synergistic behavior characterizes the other members of the class described, including but not limited to the following:

1-Ethylbutyl 5-hexynyl (4-chlorobenzyl)phosphonate; methyl 4-pentynyl phenylphosphonothionate; 2-ethoxyethyl 7-octynyl benzylphosphonate; propyl 1-methyl-2-propynyl benzylphosphonothionate; methyl 1-methyl-3-butynyl (3-chlorobenzyl)phosphonate; i-propyl 3-butynyl (4-bromobenzyl)phosphonate; 2-pentenyl 1,1-dimethyl-3-butynyl benzylphosphonate; 2,4-dimethylpentyl 3-butynyl (1-phenylpropyl)phosphonate; 2-propenyl 2-ethyl-3-butynyl (2-phenylpropyl)phosphonate; 2-methylbutyl 3-butynyl (4-iodobenzyl)phosphonate; methyl 3-methyl-4-pentynyl (2,3-dichlorobenzyl)phosphonate; 2-propenyl 1-methyl-3-butynyl (2-pyridyl)-methylphosphonate; 2-methoxypropyl 1-ethyl-2-propynyl phenylphosphonate; methyl 1-ethyl-3-butynyl benzylphosphonothionate; n-propyl (2-methyl-3-butynyl) (3-fluorobenzyl)phosphonate; i-amyl 3-butynyl (2-pyridyl)phosphonate; 2-methoxyethyl 2-propynyl phenylphosphonothionate; n-hexyl 1-ethyl-3-propynyl (4-chlorobenzyl)phosphonate; and the like.

The novel synergists of this invention may be prepared by adaptation of the synthetic procedures illustrated above, i.e. from suitable phosphonochloridates or phosphinates as well as by other known procedures. These procedures are well described in the chemical literature, for example by Kosalopoff, J.A.C.S. 72, 4292 (1950); Hudson et al, J. chem. Soc., 1859 (1960); Harman et al, U.S. Pat. No. 2,659,714; Bentov et al, J. Chem. Soc., 4750 (1964); and Cherbuliez et al, Helv. Chim. Acta, 46, 2464 (1963).

The novel synergists described herein have a degree of effectiveness not shared by certain closely related compounds. The nature and location of the unsaturated linkage has been found to have a marked effect on the synergistic effectiveness of this class of compounds. For example, reduction of the acetylenic linkage to an olefinic or a saturated linkage diminishes the synergistic activity. Displacement of the acetylenic linkage from the terminal position also decreases the activity.

The synergistic compositions of this invention may be employed to control a variety of crop pests and household pests. These compositions are not usually applied full strength, but are generally incorporated with the adjuvants and carriers normally employed for facilitating dispersion of active ingredients for insecticidal applications, recognizing the accepted fact that the formulation and mode of application may affect the activity of a material. Striking results are obtained when these compositions are applied as space sprays and aerosol sprays, for example, or are formulated into any of the diluted and extended types of formulations used in insecticidal practice, including dusts, wettable powders, emulsifiable concentrates, solutions, granulars, baits, and the like, for application to foliage, within enclosed areas, to surfaces, and wherever insect control is desired.

These synergistic compositions may be made into liquid concentrates by solution or emulsification in suitable liquids, and into solid concentrates by admixing the active components with talc, clays, and other solid carriers used in the insecticide art. Such concentrates normally contain about 5–80% of the toxic composition, and the rest inert material which includes dispersing agents, emulsifying agents, and wetting agents. For practical application, the concentrates are normally diluted with water or other liquid for liquid sprays, with liquefied propellants for aerosols, or with additional solid carrier for application as a dust or granular formulation. Baits are usually prepared by mixing such concentrates with a suitable insect food, such as mixtures of cornmeal and sugar, and insect attractants may also be present. The concentration of the active ingredients in the diluted formulations, as generally applied for control of insects, is normally in the range of about 0.001% to about 5%. Many variations of spraying and dusting compositions are well-known in the art, as are the techniques for formulating and applying these compositions.

Employing the synergistic pesticidal compositions described herein, enhanced control is obtained of both crop and household pests, including insects and acarids against which the cyclopropanecarboxylates are themselves effective, but at higher concentrations. This includes flying and crawling pests of the orders Coleoptera (beetles), Hemiptera (true bugs), Homoptera (aphids), Diptera (flies), Orthoptera (roaches), Acarina (mites and ticks), and Lepidoptera (butterflies and moths including their larvae). Because of the low mammalian toxicity of these compositions, they are preferred to compositions for use in control of pests in an environment inhabited by man and animals, including control of flies, mosquitoes, ants, roaches, moths, ticks, and the like, as well as in uses such as packaging, food and grain protection, and garden, pet, and livestock uses.

The relative amounts of synergist and chrysanthemumate employed are not critical, in that a relatively minor amount, e.g., less than one part of synergist per part of chrysanthemumate, is effective in imparting a beneficial effect to the combination. From practical considerations, it is preferred to use larger amounts of synergist, for example, from 2 to 50 parts of synergist per part of cyclopropanecarboxylate. Even larger proportions of synergist may be employed without detriment, whether or not the optimum synergistic proportions have been achieved. It is clear that effective amounts of synergist should be employed in the compositions, that the components should be present in synergistic proportions, and that effective amounts of the compositions, to control the particular insect pests in the environment of infestation, should be applied.

It is apparent that many modifications may be made in the formulation and application of the compositions of this invention, without departing from the spirit and scope of the invention, and of the following claims:

1. An insecticidal composition comprising an insecticidally effective amount of a combination of
    A. 3-phenoxybenzyl 2,2-dimethyl-3-(2,2-dichlorovinyl)cyclopropanecarboxylate the insecticidal activity of which is synergized by
    B. a synergistically effective amount of a compound of the formula

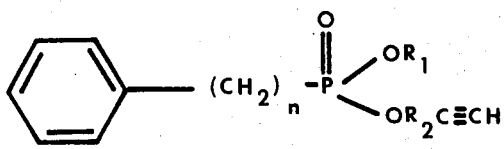

wherein $n$ is 0 or 1, $R_1$ is selected from the group consisting of alkyl and alkenyl having one to six carbon atoms; and $R_2$ is alkylene of one to four carbon atoms; wherein the ratio of A:B is in the range of 1:0.5 and 1:20.

2. The insecticidal composition of claim 1 wherein $n$ is 1.

3. The insecticidal composition of claim 1 wherein $n$ is 0.

4. The insecticidal composition of claim 3 wherein $R_1$ and $R_2$ each contain three to four carbon atoms.

5. The insecticidal composition of claim 4 wherein the synergist is isobutyl 2-propynyl phenylphosphonate or propyl 2-propynyl phenylphosphonate.

6. The insecticidal composition of claim 4 wherein the synergist is isobutyl 2-propynyl phenylphosphonate.

7. A method of controlling insects which comprises applying thereto an insecticidally effective amount of a composition comprising:
    A. 3-phenoxybenzyl 2,2-dimethyl-3-(2,2-dichlorovinyl)cyclopropanecarboxylate the insecticidal activity of which is synergized by
    B. a synergistically effective amount of a compound of the formula

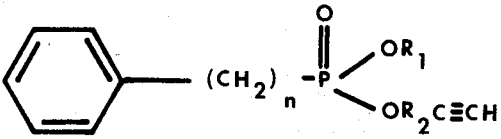

wherein $n$ is 0 or 1, $R_1$ is selected from the group consisting of alkyl and alkenyl having one to six carbon atoms; and $R_2$ is alkylene of one to four carbon atoms; wherein the ratio of A:B is in the range of 1:0.5 and 1:20.

8. The method of claim 7 wherein $n$ is 1.

9. The method of claim 7 whrein $n$ is 0.

10. The method of claim 9 wherein $R_1$ and $R_2$ each contain three to four carbon atoms.

11. The method of claim 10 wherein the synergist is isobutyl 2-propynyl phenylphosphonate or propyl 2-propynyl phenylphosphonate.

12. The method of claim 11 wherein the synergist is isobutyl 2-propynyl phenylphosphonate.

* * * * *

UNITED STATES PATENT OFFICE
CERTIFICATE OF CORRECTION

PATENT NO. : 3,944,666

DATED : March 16, 1976

INVENTOR(S) : Ronald E. Montgomery and Harry H. Incho

It is certified that error appears in the above-identified patent and that said Letters Patent are hereby corrected as shown below:

The second from the last line of the title should read: "ALKENYL) MONO OMEGA-ALKYNYL".

Column 1, line 8, should read: "(ALKYL AND ALKENYL) MONO".

Column 1, line 38, change "supply pf..." to "supply of...".

Column 2, at the end the following should be inserted: "class of esters includes the pyrethrins, allethrin (3-allyl-2-methyl-4-oxo-2-cyclopentenyl chrysanthemumate) and related insecticides as described by Schechter and La Forge in U.S. Patent 2,661,374; cyclethrin (3-(2-".

Column 3, delete lines 69 and 70.

Column 4, delete lines 1 and 2.

Column 4, line 42, change "colume", to "volume".

Column 7, line 29, change "3.4 g2-propyn-1-ol" to "3.4g 2-propyn-1-ol".

Column 11, line 50, correct "(1-cyclohexene" to "(1-Cyclohexene"

Column 12, line 62, should read "themumate(A)".

Column 12, line 63, delete "A)".

Column 12, line 64, change "compo-" to "Compo-".

Column 13, line 5, should read "themumate(A)".

Column 13, line 6, delete "A)".

UNITED STATES PATENT OFFICE
CERTIFICATE OF CORRECTION

PATENT NO. : 3,944,666

DATED : March 16, 1976

INVENTOR(S) : Ronald E. Montgomery and Harry H. Incho

It is certified that error appears in the above-identified patent and that said Letters Patent are hereby corrected as shown below:

Column 13, line 7, change "compo-" to "Compo-".

Column 13, line 15, should read "phenylphosphonate".

Column 13, line 18, should read "phenylphosphonate".

Column 15, line 57, change "1-ethyl-3-propynyl" to "1-ethyl--propynyl".

Column 15, line 65, change "J. chem. Soc." to "J. Chem. Soc.".

Signed and Sealed this

Twenty-first Day of September 1976

[SEAL]

Attest:

RUTH C. MASON
Attesting Officer

C. MARSHALL DANN
Commissioner of Patents and Trademarks